United States Patent [19]

Puckett et al.

[11] Patent Number: 5,703,131
[45] Date of Patent: Dec. 30, 1997

[54] METHOD FOR THE DETOXIFICATION OF MUSTARD GAS SULFUR-CONTAINING QUATERNARY AMMONIUM IONENE POLYMERS AND THEIR USE AS MICROBICIDES

[75] Inventors: Wallace E. Puckett; Mark L. Zollinger; Fernando Del Corral, all of Memphis, Tenn.

[73] Assignee: Buckman Laboratories International Inc., Memhis, Tenn.

[21] Appl. No.: 529,711

[22] Filed: Sep. 18, 1995

Related U.S. Application Data

[60] Continuation of Ser. No. 359,732, Dec. 20, 1994, abandoned, which is a division of Ser. No. 993,079, Dec. 18, 1992, Pat. No. 5,387,717, which is a continuation-in-part of Ser. No. 928,356, Aug. 12, 1992, Pat. No. 5,401,881.

[51] Int. Cl.$^6$ .......................... A01N 33/12; C07C 211/63; C07C 215/40; C07C 209/12
[52] U.S. Cl. .......................... 514/642; 504/100; 504/160; 564/292; 564/295; 564/296; 588/200; 588/206
[58] Field of Search ................... 588/200, 206; 564/292, 295, 296, 100, 160; 514/642

[56] References Cited

U.S. PATENT DOCUMENTS

| | | | |
|---|---|---|---|
| 4,217,914 | 8/1980 | Jacquet et al. | 132/7 |
| 4,874,532 | 10/1989 | Worley | 210/755 |

FOREIGN PATENT DOCUMENTS

299706A7  5/1992  Germany.

OTHER PUBLICATIONS

Chemical Abstracts, vol. 112, No. 15, Abstract No. 133993d (Apr. 9, 1990).

*Primary Examiner*—Peter O'Sullivan
*Attorney, Agent, or Firm*—Armstrong, Westerman, Hattori, McLeland & Naughton

[57] ABSTRACT

A method for the detoxification of a mustard gas by reaction with a bis-tertiary diamine resulting in quaternary ammonium ionene polymers. Sulfur-containing quaternary ammonium ionene polymers which are useful as microbicides for controlling the growth of microorganisms in aqueous systems and on surfaces, as well as for inhibiting slime formation in aqueous systems and biocidal compositions contain effective amounts of the sulfur-containing quaternary ammonium ionene polymers.

3 Claims, No Drawings

METHOD FOR THE DETOXIFICATION OF MUSTARD GAS SULFUR-CONTAINING QUATERNARY AMMONIUM IONENE POLYMERS AND THEIR USE AS MICROBICIDES

This application is a continuation of application Ser. No. 08/359,732, filed Dec. 20, 1994 now abandoned, which is a divisional of application Ser. No. 07/993,079, filed Dec. 18, 1992, now U.S. Pat. No. 5,387,717, which is a continuation-in-part of application Ser. No. 07/928,356 filed Aug. 12, 1992, now U.S. Pat. No. 5,401,881.

This invention relates to a method for the detoxification of mustard gases by reacting a mustard gas with a bis-tertiary diamine to form a quaternary ammonium ionene polymer. The invention also relates to sulfur-containing quaternary ammonium ionene polymers and their use as microbicides. New sulfur-containing quaternary ammonium ionene polymers are described, as well as methods for their preparation. Microbicidal compositions and methods for inhibiting the growth of microorganisms employing sulfur-containing quaternary ammonium ionene polymers are also disclosed.

2,2'-dichloroethyl sulfide, commonly referred to as mustard gas or mustard, was first used by the Germans during World War I. It is a heavy, oily liquid and is nearly colorless and odorless when pure. Other compounds such as $(ClCH_2CH_2)_2NEt$, $(ClCH_2CH_2)_2NMe$ and $(ClCH_2CH_2)_3N$ also fall within the class of compounds known and used as mustard gases. Even today, with the availability of more advanced chemical technologies, mustard gas may still be the war gas of choice due largely to its ease of manufacture.

Mustard gas is classified as a vesicant or blistering agent, and it is described as both persistent and an irritant. Exposure, even at very low concentrations, can cause skin and eye damage. At higher concentrations, mustard gas is often lethal. Mustard gas is a known carcinogen. In *Principles and Methods of Toxicology*, by A. Wallace Hayes, mustard gas is listed as Ames positive, as well as positive on in vivo tumor assays on humans and mice.

Although an accurate accounting of nerve agents is not available due to security considerations, it is safe to say that the U.S. government has on hand many tons of mustard gas, both as munitions and in bulk containers. In the Department of Defense Authorization Act of 1986, Public Law 99–145 was enacted to dispose of all U.S. stockpiles of unitary chemical weapons. The law mandates that safe and adequate facilities be designed to achieve the objective of maximum safety. Specifically, the law provides that the disposal facilities must be created and disposal accomplished such that the environment, the public at large, and the personnel involved in the disposal are protected as much as possible. Lastly, the disposal facilities must be detoxified and then dismantled.

It has been decided that the method of choice in the United States for the disposal of chemical stockpiles would be by incineration. There are several patents or papers in the open literature which describe various methods of detoxification of mustard gas. Most of these involve variations on the basic theme of incineration, although there is some work involving reaction of mustard with monomethylamine (Edgewood Technical Report EM-TR-76041). This procedure involves the disposal of only small quantities of mustard gas, which were contained in field kits used by the U.S Army for the identification of mustard gas use on the battlefield.

Another chemical method for the detoxification of mustard is by Yu-Chu Yang et al., *J. Org. Chem.* 1990, 55, 3664–66. The method of Yang et al. reacts mustard gas with some N-sulfonyloxaziridine derivatives, to form the sulfoxide form of mustard gas. U.S. Pat. No. 4,949,641 describes a method for detoxification of mustard gases by reacting with incandescent pyrophoric metallic powder, preferably aluminum.

The present invention relates to the reaction of a mustard gas with various bis-tertiary diamines, such as N,N,N',N'-tetramethylethylene diamine, to form a quaternary ammonium ionene polymer. When the mustard gas is 2,2'-dichloroethyl sulfide this reaction yields a sulfur-containing quaternary ammonium ionene polymer. The molecular weight of these polymers is preferably approximately 2,000 and the toxicological profile in vivo indicates that these polymers can be much less carcinogenic than mustard gas.

The use of the sulfur-containing quaternary ammonium ionene polymers resulting from the detoxification reaction as microbicides in water treatment and on surfaces is also described here. These polymers according to the invention can show less toxicity toward fish than other ionene polymers already being sold as water treatment chemicals.

A large number of commercial, industrial, agricultural, and wood products are subject to microbiological attack which reduces or destroys their economic value. Examples of materials that may be subject to microbiological degradation are surface coatings, wood, agricultural seed, leather and plastics, including flexible plastics.

The temperature at which these products are stored and their intrinsic characteristics make these products susceptible to the growth of microorganisms. These microorganisms can be introduced during the manufacturing of these products by exposure to air, tanks, pipes, equipment, and humans and/or during their use from multiple openings and reclosures of packaged products and by the introduction of contaminated objects to stir or remove material.

Aqueous systems containing organic materials are also highly subject to microbiological attack. Such aqueous systems include latexes, surfactants, dispersants, stabilizers, thickeners, adhesives, starches, waxes, proteins, emulsifying agents, detergents, cellulose products, agricultural irrigation fluids, and resins formulated in aqueous solutions, emulsions or suspensions.

These systems frequently contain relatively large amounts of water causing them to be well-suited environments for microbiological growth and, thus, attack and degradation. Microbiological degradation of aqueous systems containing organic materials may manifest itself as a variety of problems, such as loss of viscosity, gas formation, objectionable odors, decreased pH, emulsion breaking, color change, and gelling.

Another objectionable phenomenon occurring in industrial process systems involving water is slime formation. Slime consists of matted deposits of microorganisms, fibers and debris. It may be stringy, pasty, rubbery, tapioca-like, or hard, and may have a characteristic undesirable odor that is different from that of the liquid suspensions in which it is formed.

The microorganisms primarily involved in slime formation are different species of spore-forming and nonspore-forming bacteria, in particular capsulated forms of bacteria which secrete gelatinous substances that envelop or encase the cells. Slime microorganisms also include filamentous bacteria, filamentous fungi of the mold type, yeasts, and yeast-like organisms. Slime reduces yields in paper production and causes plugging and other problems in water systems.

In addition, different types of water, both potable and nonpotable, need disinfectants to keep them from being spoiled by microorganisms. In the United States, the most common method of disinfection is the use of chlorination.

Chlorination, however, can be accompanied by some disadvantages, such as chlorine gas explosion or leakage, during water treatment, and may result in the formation of toxic halocarbons, such as chloroform and others. In this respect, variety of compounds are used as replacements for chlorine treatment, including ozone, chlorine dioxide, bromine, potassium permanganate, p-chlorosulfamidobenzoic acid, cyanuric acid derivatives, isocyanuric acid derivatives, quaternary ammonium compounds, and various chloramine compounds.

Quaternary ammonium ionene polymers belong to a class of compounds, which, together with methods for their preparation, are described in U.S. Pat. Nos. 3,874,870, 3,931,319, 4,025,627, 4,027,020, and 4,506,081, as well as the references cited in these patents. These polymers are often used as microbicides. The disclosure of each of these patents is incorporated herein by reference.

Certain sulfur-containing quaternary ammonium ionene polymers and methods to prepare them are also known. U.S. Pat. No. 4,046,750 describes an ionene polymer containing a sulfur diradical, —S—, which is used to modify polymeric beads for use in binding a diverse group of small and large anionic compounds in separation, analytical, diagnostic and clinical applications. U.S. Pat. No. 4,217,914 describes sulfur-containing quaternary ammonium ionene polymers which have divalent sulfur-containing radicals, —S—, —S—S—, —SO— and —SO$_2$—, and their use in cosmetic compositions. The disclosure of each of these patents is incorporated herein by reference.

One object of the present invention is to provide a safe method for the detoxification of mustard gas. Another object of the present invention is to provide new sulfur-containing quaternary ammonium ionene polymers which are useful as microbicides. A third object is to provide a microbicidal composition employing a sulfur-containing quaternary ammonium ionene polymer as an active ingredient. Providing a method for inhibiting the growth of microorganisms in aqueous fluid systems or on surfaces using a sulfur-containing quaternary ammonium ionene polymer is also an object of this invention. Other objects of this invention will be apparent from the description of the invention below or from the practice of the invention.

These and other objects may be accomplished by:

a method for the detoxification of a mustard gas comprising the step of contacting a mustard gas with a bis-tertiary diamine to form a quaternary ammonium ionene polymer;

a sulfur-containing quaternary ammonium ionene polymer comprising a repeating unit of formula I:

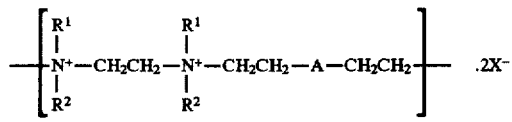

wherein X$^-$ is a counter-ion; R$^1$ and R$^2$, which can be the same or different, are selected from a lower alkyl group and —CH$_2$CH$_2$OH; and A is a radical selected from —S—, —S—S—, —S—CH$_2$CH$_2$—S— and the oxidation products of —S—, —S—S—, and of —S—CH$_2$CH$_2$—S—;

a microbicidal composition comprising an aqueous solution of a sulfur-containing quaternary ammonium ionene polymer comprising a repeating unit of formula II:

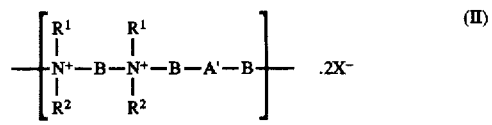

wherein X$^-$ is a counter-ion; R$^1$ and R$^2$, which can be the same or different, are selected from a lower alkyl group and —CH$_2$—CH$_2$—OH; A' is a radical selected from —S—, —S—CH$_2$CH$_2$—S—, —S—S— and the oxidation products of —S—, of —S—CH$_2$CH$_2$—S— and of —S—S—; and B is a radical selected from C$_1$-C$_5$ alkyl, —CH$_2$—CH(OH)—CH$_2$—, and —(CH$_2$)$_m$—O—(CH$_2$)$_m$—, where each m is independently 1, 2, or 3, in an amount effective to inhibit the growth of at least one microorganism;

a method for inhibiting the growth of at least one microorganism in an aqueous system comprising the step of adding to an aqueous system in recognized need thereof, in an amount effective to inhibit the growth of the microorganism, the sulfur-containing quaternary ammonium polymer comprising a repeating unit of formula II, above;

a method for inhibiting slime formation in an aqueous system comprising the step of adding to an aqueous system in recognized need of such inhibition a sulfur-containing quaternary ammonium polymer comprising a repeating unit of formula II, above; and a method for inhibiting the growth of microorganisms on the surface of a substance comprising the step of applying to the surface in recognized need of such inhibition a sulfur-containing quaternary ammonium polymer comprising a repeating unit of formula II, above.

In a first embodiment this invention provides a method for the detoxification of a mustard gas comprising the step of contacting a mustard gas with a bis-tertiary diamine to form a quaternary ammonium ionene polymer. Mustard gases, such as those discussed above and particularly 2,2'-dichloroethyl sulfide, can react readily with a bis-tertiary diamine to form a quaternary ammonium ionene polymer which can be significantly less toxic the original mustard gas. Additionally, as described in other embodiments of this invention, when the mustard gas is 2,2'-dichloroethyl sulfide, the sulfur-containing quaternary ammonium ionene polymers made by this detoxification reaction are useful as safe and effective microbicides.

The detoxification reaction can be carried out with any bis-tertiary diamine. The bis-tertiary diamine can be symmetrical or asymmetrical as shown, for example, by substituents R$^1$, R$^2$ and/or B in formulae I and II below. A preferred bis-tertiary diamine is N,N,N',N'-tetramethylethylene diamine (TMEDA).

The detoxification reaction may be carried out in the presence or absence of a solvent. Any suitable solvent can be used as the medium for the reaction. Aqueous solvent systems, particularly water itself, are preferred as they also function as solvents for the ionene polymer produced by the reaction. The reaction is also preferably carried out above room temperature at temperatures ranging from 50°–90° C., most preferably at approximately 60° C.

The ionene polymers resulting from the detoxification of mustard gas are included in those of formulae I and II discussed below. The polymers generally have molecular weights of about 2000 and have been found to be effective and safe microbicides.

The present invention also provides novel sulfur-containing quaternary ammonium ionene polymers comprising a repeating unit of formula I:

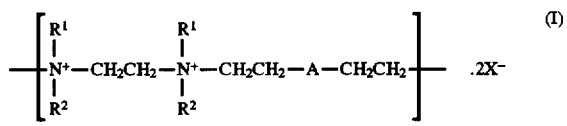

wherein $X^-$ is a counter-ion; $R^1$ and $R^2$, which can be the same or different, are selected from a lower alkyl group and —$CH_2CH_2OH$; and A is a radical selected from —S—, —S—$CH_2CH_2$—S— and the oxidation products of —S—, and of —S—$CH_2CH_2$—S—.

The counter-ion, $X^-$, may be a monovalent anion or $2X^-$ may be a divalent anion. Preferably, X is a halogen anion; more preferably, chloride.

The substituents $R^1$ and $R^2$ are lower alkyl groups or —$CH_2CH_2OH$, preferably $C_1$–$C_4$ alkyl groups. More preferably, these substituents are methyl or ethyl groups. As employed here, and throughout this disclosure, the term "alkyl" includes both straight chain and branched alkyl groups.

A is a radical selected from —S—, —S—$CH_2CH_2$—S— and the oxidation products of —S—, and of —S—$CH_2CH_2$—S—. The oxidation products of the sulfur-containing radical A are those products obtained by oxidizing the sulfur atoms within each radical. For example, the oxidation products resulting from the oxidation of an ionene polymer when A is —S—, are ionene polymers where A is —SO— after a first oxidation and where A is —$SO_2$— after a second oxidation. As described below, it is possible to control the amount of oxidation to obtain ionene polymers having the sulfur atoms within the sulfur-containing radical A at a desired oxidation state. The sulfur-containing radical A is preferably —S—, —SO—, or —$SO_2$— and more preferably —SO— or —$SO_2$—.

The molecular weight of the sulfur-containing quaternary ammonium ionene polymers preferably ranges from 1,000–5,000, more preferably 1,000–3,000 and most preferably 1500.

In a preferred embodiment, X is chloride; $R^1$ and $R^2$ are each methyl; A is —S—, —SO—, or —$SO_2$—; and the polymer has a molecular weight of about 1500.

In general, the sulfur-containing ionene polymers of formula I can be prepared by reacting a suitable bis-tertiary diamine, such as tetramethylenediamine (TMEDA), with an appropriate dihaloalkyl sulfide, e.g. 2,2'-dichloroethyl sulfide, at a preferred temperature of 50°–90° C., more preferably about 60° C., for several hours in water. The reaction can proceed cleanly, with no side products formed, to advantageously yield a polymer-in-water solution that may be used as is or diluted to an appropriate strength. In such a case, no further workup is required.

To obtain sulfur-containing quaternary ammonium ionene polymers having sulfur-containing radicals where the sulfur atoms are oxidized, the ionene polymer product solution is oxidized by means known in the art, such as by reaction with hydrogen peroxide. The degree of oxidation is controlled by the reaction stoichiometry. Completion of the oxidation can be monitored by tests for the presence of peroxide as is known in the art, such as a starch/iodine test. This oxidation reaction also proceeds cleanly giving a polymer-in-water solution that may be used as is or diluted to an appropriate strength without further workup.

An alternative preparation for oxidized sulfur-containing quaternary ammonium ionene polymers is to react a suitable bis-tertiary diamine with an oxidized dihaloalkyl sulfide, such as the sulfoxide described by Yu-Chu Yang et al., *J. Org. Chem.* 1990, 55, 3664–66. This preparation, starting with the oxidized dihaloalkyl sulfide, is accomplished in the same manner described above for the reaction between a bis-tertiary diamine and a dihaloalkyl sulfide described above.

The present invention is also directed to the use of sulfur-containing quaternary ammonium ionene polymers comprising a repeating unit of formula II:

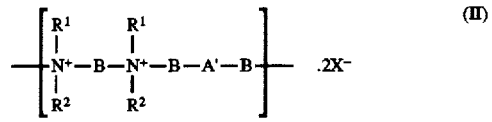

as microbicides. In these polymers, $X^-$, $R^1$, and $R^2$ are the same as defined above for the a repeating unit of formula I.

A' is a radical selected from —S—, —S—$CH_2CH_2$—S—, —S—S— and the oxidation products of —S—, of —S—$CH_2CH_2$—S— and of —S—S—. The oxidation products may be obtained in the same manner as those of formula I. Preferably A' is —S—, —SO—, —$SO_2$—, or —$SO_2$—S— and more preferably —SO— or —$SO_2$. The preparation of some sulfur-containing quaternary ammonium ionene polymers of formula II where A' is —S—, —S—S—, —SO—, —$SO_2$— is described in U.S. Pat. No. 4,217,914 and is incorporated herein by reference.

B is a radical selected from $C_1$–$C_5$ alkyl, —$CH_2$—CH(OH)—$CH_2$—, and —$(CH_2)_m$—O—$(CH_2)_m$—, where each m is independently 1, 2, or 3. Preferably, B is a $C_1$–$C_3$ alkyl and more preferably an ethyl group.

The molecular weight of the ionene polymers preferably ranges from 1,000–5,000. A more preferred range is 1,000–3,000. Most preferably, the molecular weight is about 1500.

The sulfur-containing quaternary ammonium ionene polymers of the present invention are effective microbicides against microorganisms such as bacteria, algae and fungi. It has been found that sulfur-containing quaternary ammonium ionene polymers are particularly useful for inhibiting the growth of such microorganisms in aqueous systems. Thus, the present invention. relates to a method of inhibiting the growth of at least one microorganism in an aqueous system comprising the step of adding to an aqueous system in recognized need of such inhibition a sulfur-containing quaternary ammonium ionene polymer in an amount effective to inhibit the growth of at least one microorganism. Representative aqueous systems include aqueous solutions, emulsions and suspensions as described above. Specific preferred systems are metalworking fluids.

Sulfur-containing quaternary ammonium ionene polymers have also been found to be useful for inhibiting the formation of slime in an aqueous system. The present invention, then, also relates to a method for inhibiting the formation of slime in aqueous systems comprising the step of adding to an aqueous system in recognized need of such inhibition a sulfur-containing quaternary ammonium ionene polymer in an amount effective to inhibit the formation of slime. This method is effective in aqueous systems such as a pulp slurry or liquids used in a water cooling device.

A further use of sulfur-containing quaternary ammonium ionene polymers according to the present invention resides in a method for inhibiting the growth of at least one microorganism on a substance susceptible to deterioration or disfigurement by microorganisms or metabolic products of microorganisms. The method comprises the step of applying to a surface in recognized need thereof or admixing with the substance forming the surface, a sulfur-containing quaternary ammonium ionene polymer in an amount effective to inhibit the growth of at least one microorganism. This method is effective on substances such as wood, surface coatings (i.e. paint films), leather, agricultural seed, man-made or naturally occurring polymers (including flexible plastic) and the like. This method of inhibiting the growth of microorganisms on surfaces achieves the desired inhibition for significant periods of time. The microorganisms whose growth are inhibited include, for example, fungi. Additionally, the sulfur-containing quaternary ammonium ionene polymers described here are effective contact disinfectants.

The present invention also relates to biocidal compositions comprising an effective amount of a sulfur-containing quaternary ammonium ionene polymer in an aqueous solution. The biocidal composition can contain other additives such as surfactants and defoamers, for example, as are known in the art. A biocidal composition containing a sulfur-containing quaternary ammonium ionene polymer can be used in any of the methods described above.

According to the present invention, inhibition of the growth of at least one microorganism or of slime formation encompasses the prevention, control and/or reduction of that growth or formation. Therefore, for example, the inhibition of the growth of at least one microorganism in an aqueous fluid can be achieved by preventing such growth in the first instance, preventing or controlling further growth if such has already occurred, and/or reducing the amount of any existing growth.

The use of sulfur-containing quaternary ammonium ionene polymers as microbicides has a number of advantages. They are hydrolyrically stable over a wide pH range, i.e. pH 3–11. They are also soluble in many solvents, such as water, small chain alcohols and some polar organic solvents, and therefore may be readily diluted for convenience of use Their compatibility, low color, and efficiency makes them advantageous for use as microbicides in man-made or naturally occurring polymers and for impregnation in or application on surfaces such as wood, paper, or other materials.

The sulfur-containing quaternary ammonium ionene polymers may, of course, be applied in various ways—incorporated into a coating or composition, applied as dust by mixing with powdered diluents, dissolved in a solvent or in water and then emulsified and dispersed into a non-solvent. The particular use desired will generally dictate the method of application.

The effective amount or percentage of active compound necessary to achieve the desired result will vary somewhat depending on the substrate to be protected, the conditions for algal, bacterial or fungal growth, and the degree of protection desired. For the treatment of surfaces or materials, the concentration of a sulfur-containing quaternary ammonium ionene polymer according to the present invention preferably ranges from about 0.01 to 0.5 ppm (w/w); more preferably from 0.01 to 0.1 ppm, and most preferably from 0.01 to 0.025 ppm in the composition applied.

In aqueous systems, a preferred effective amount of active compound ranges from 0.05 to 5000 ppm, and more preferably, from 0.05 to 1000 ppm of the aqueous system. The amount of sulfur-containing quaternary ammonium ionene polymer effective to prevent the formation of slime in an aqueous liquid preferably ranges from 10 to 100 ppm, and more preferably, from 5 to 25 ppm of the aqueous liquid.

To illustrate the nature of the invention, the following examples are given. It should be understood, however, that the invention is not to be limited to the specific conditions or details set forth in these examples.

EXAMPLE 1

Detoxification of Mustard Gas: Preparation of poly[thioethylene(dimethyliminio)ethylene(dimethyliminio)ethylene].

To a 110 ml single neck round bottom flask, with reflux condenser, magnetic stirrer, and $N_2$ blanket were added 11.5 g. N,N,N',N'-tetramethylethylene diamine (TMEDA), 15.8 g 2,2'-dichlorodiethylsulfide (Mustard Gas), and 25 ml $H_2O$. This dispersion was then mixed and heated to 60° C. for 8 hours. The solution gradually took on a reddish cast and the reaction mixture was then cooled to room temperature.

EXAMPLE 2

Detoxification of Mustard Gas: Preparation of poly[sulfoxyethylene(dimethyliminio)ethylene(dimethyliminio)ethylene]

To a 100 ml single neck round bottom flask, with reflux condenser, magnetic stirrer, and $N_2$ blanket were added 11.5 g. N,N,N',N'-tetramethylethylene diamine (TMEDA), 15.8 g. 2,2'-dichlorodiethylsulfide (Mustard Gas), and 25 ml $H_2O$. This dispersion was then mixed and heated to 60° C. for 8 hours. The solution gradually took on a reddish cast and the reaction mixture was then cooled to room temperature. A slow addition of 11.3 of 30% hydrogen peroxide was effected in such a manner that the temperature never exceeded 60° C. The solution was again cooled to room temperature, after a short mixing time, to afford a 51% solution, by weight, of polymer.

EXAMPLE 3

The polymer produced in Example 1 was studied to determine its potential carcinogenicity using a standard Ames test. Table provides the results of the test vs. a list of organisms used in an Ames test for mutagenicity.

TABLE 1

| Organism | Test Result |
| --- | --- |
| TA 98 | Negative response |
| TA 100 | Negative response |
| *TA 1535 | Slight positive |
| TA 1537 | Negative response |

*Confirmatory test for this strain was inconclusive.

EXAMPLE 4

Preparation of poly [thioethylene (dimethyliminio) ethylene (dimethyliminio) ethylene], (Compound 1).

A solution of 17.4 g TMEDA (0.15 moles), 23.85 g 2,2'-dichloroethyl sulfide (0.15 moles), and 25.76 g water was prepared in a reactor. The contents were heated to 60° C. for seven and one-half hours, with continuous mixing. After two hours, the contents were in a single, aqueous phase. The reactor was then allowed to cool to room temperature. The product polymer-in-water solution was diluted to an appropriate concentration and used in the Examples below.

EXAMPLE 5

Preparation of poly[sulfoxyethylene(dimethyliminio) ethylene (dimethyliminio)ethylene], (Compound 2)

A solution of 17.4 g TMEDA (0.15 moles), 23.85 g 2,2'-di-chloroethyl sulfide (0.15 moles), and 25.76 g water was prepared. The contents of the reactor were heated to 60° C. for seven and one-half hours, with continuous mixing. After two hours, the contents were in a single, aqueous phase. The reactor was then allowed to cool to room temperature.

17.0 g of a 30% solution of hydrogen peroxide were then added portion-wise to the reaction flask. After four hours, a standard starch/iodine test for peroxide indicated a negative result. The product polymer-in-water solution was diluted to an appropriate concentration and used in the Examples below.

EXAMPLE 6

The effect of sulfur-containing quaternary ammonium ionene polymers on the bacteria *Enterobacter aerogenes* and/or *Pseudomesas aeruginosa* and the effect on algae were determined using the method described in U.S. Pat. No. 2,881,070 (the disclosure of which is incorporated herein by reference). The results are described in Table 2 and Table 3.

TABLE 2

Concentration in parts per million (ppm) required for 90% or greater kill of the ionene polymers, Compounds 1 and 2, against the bacteria *Enterobacter aerogenes* and *Pseudomonas aeruginosa* at pH 6 and pH 8 in a basal salt substrate after 18 hours contact.

| Compound | Bacterium | pH 6 | pH 8 |
|---|---|---|---|
| 1 | *Enterobacter aerogenes* | 0.5 | 0.05 or less |
| 1 | *Pseudomonas aeruginosa* | 0.7 | 0.5 |
| 2 | *Enterobacter aerogenes* | 0.7 | 0.5 |

TABLE 3

Minimum Inhibitory Concentration of the ionene polymers of Compounds 1 and 2 in parts per million (ppm) against the algae *Chlorella pyrenoidosa*, *Chlorococcum hypnosporum* and *Oscillatoria proliffera* at pH 7 in a basal salt substrate after 28 days contact.

| Algae | Compound 1 | Compound 2 |
|---|---|---|
| *Chlorella pyrenoidosa* | 5.0 | 2.0 |
| *Chlorococcum hypnosporum* | 1.0 | 2.0 |
| *Oscillatoria proliffera* | 5.0 | 1.0 |

EXAMPLE 7

Determination of the Zone of Inhibition of the Ionene Polymer Compound 1 Against Various Fungi The technique utilized was a standard agar diffusion method in which biological activity of the test chemical is expressed as a zone of inhibition encircling the point of application. In the test, paper discs (6 mm diameter) were dipped in aqueous solutions of the ionene polymer, respectively containing $10^3$, $10^4$ and $10^5$ ppm of the active ingredient. After briefly air drying, the treated discs were placed at the center of potato dextrose agar plates freshly streaked with one of several species of the organisms listed in Table 3. Following incubation for ten days, the zone diameters were determined, with the results listed in Table 4.

TABLE 4

Zone of inhibition, in millimeters, of *Aspergillus niger*, *Trichoderma harzianum*, *Penicillum roqueforti*, and *Aureobasidium pullulans* versus the ionene polymer concentrations used.

| Ionene concentration ppm: Organism | $10^3$ | $10^4$ | $10^5$ |
|---|---|---|---|
|  | Zone diameter (mm) | | |
| *Aspergillus niger* | 0 | 0 | 18 |
| *Trichoderma Harzianum* | 0 | 0 | 6 |
| *Penicillium roqueforti* | 8 | 14 | 25 |
| *Aureobasidium pullulans* | 0 | 10 | 15 |

EXAMPLE 8

The effectiveness of sulfur-containing quaternary ammonium ionene polymer compositions as contact disinfectants in short contact suspension screens was examined using a mixed bacterial population comprised of *Staphylococcus aureus*, *Enterobacter aerogenes* and *Pseudonomas aeruginosa*. Each microorganism was grown in Tryptone Glucose extract agar (TGEA) and harvested after 24 hours. A bacterial suspension was prepared in saline with each organism and adjusted by aid of a McFarland ™1 turbidity Standard to equal approximately $1.0 \times 10^8$ cell/ml. Equal portions of each adjusted bacterial suspension were mixed and employed as the inoculum. The day of the assay a freshly prepared stock solution of the biocide was made up (1%) and diluted to the desired concentration in sterile distilled water. Ten (10.0) milliliters of the diluted biocide were dispensed in sterile test tubes and 20 microliters of the inoculum were introduced and timed for exactly 10.0 minutes. After exposure, each 1.0 milliliter was transferred to 9 milliliters of a biocide deactivating solution. After the deactivation, serial tenfold dilutions were prepared in 9 ml sterile saline blanks. Bacterial survivors were estimated by standard pour platting technique employing TGEA. All plates were incubated at 37° C. for 48 hours and counted. Controls were treated similarly with the exception that no biocide was used, only sterile distilled water.

The results are shown below in Table 5. Both compounds 1 and 2 have fast acting antibacterial action equal to or better than Benzalkonium Chloride (Ben.Cl), a quaternary ammonium salt routinely employed for sanitizing and disinfecting.

TABLE 5

Short contact efficacy of Compounds 1, 2 and Benzalkonium Chloride
% REDUCTION (10 min exposure)

| Compound | Concentration (ppm) | | | |
|---|---|---|---|---|
|  | 50 | 100 | 250 | 500 |
| 1 | 99.91 | 99.93 | 99.93 | 99.95 |
|  | 99.98 | 99.99 | 99.99 | 99.98 |
| 2 | 96.99 | 97.47 | 97.15 | 98.53 |
| Ben.Cl | 83.44 | 86.29 | 99.68 | 99.99 |

The invention claimed is:

1. A microbicidal composition comprising an aqueous solution containing a sulfur-containing quaternary ammonium ionene polymer comprising a repeating unit of formula II:

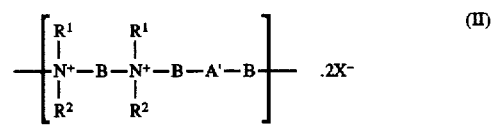

wherein $X^-$ is a counter-ion; $R^1$ and $R^2$, which can be the same or different, are selected from a lower alkyl group and —$CH_2$—$CH_2$—OH; A' is a radical selected from —S—, —S—$CH_2CH_2$—S—, —S—S— and the oxidation products of —S—, of —S—$CH_2CH_2$—S— and of —S—S—; and B is a radical selected from $C_1$-$C_5$ alkyl, —$CH_2$—CH(OH)—$CH_2$—, and —$(CH_2)_m$—O—$(CH_2)_m$—, where each m is independently 1, 2, or 3, wherein said sulfur-containing quaternary ammonium ionene polymer has a molecular weight of from 1,000 to 3,000, and wherein said sulfur-containing quaternary ammonium ionene polymer is present in an amount of from 0.05 ppm to 1,000 ppm in said aqueous solution.

2. The microbicidal composition of claim 1 wherein A' is selected from —S—, and the oxidation products —SO—, —$SO_2$— and —$SO_2$—S—.

3. The microbicidal composition of claim 2 wherein the quaternary ammonium ionene polymer is selected from poly[thioethylene-(dimethyliminio) ethylene-(dimethyliminio)ethylene]and poly [sulfoxyethylene-(dimethyliminio)ethylene-(dimethyliminio)ethylene].

* * * * *

UNITED STATES PATENT AND TRADEMARK OFFICE
CERTIFICATE OF CORRECTION

PATENT NO.: 5,703,131
DATED : December 30, 1997
INVENTOR(S): PUCKETT et al.

It is certified that error appears in the above-identified patent and that said Letters Patent is hereby corrected as shown below:

On the title page, item [73],
The assignee address [73] should read --Memphis--.

Column 3, line 57, please delete ".2X⁻" and replace it with -- · 2X⁻--.

Column 4, line 3, please delete ".2X⁻" and replace it with -- · 2X⁻--.

Column 5, line 4, please delete ".2X⁻" and replace it with -- · 2X⁻--.

Column 6, line 9, please delete ".2X⁻" and replace it with -- · 2X⁻--.

IN THE CLAIMS:

In claim 1, line 49, please delete ".2X⁻" and replace it with -- · 2X⁻--.

Signed and Sealed this

Twenty-first Day of April, 1998

Attest:

BRUCE LEHMAN

*Attesting Officer*     *Commissioner of Patents and Trademarks*